United States Patent [19]
Domenico et al.

[11] Patent Number: 5,126,556
[45] Date of Patent: Jun. 30, 1992

[54] BOTTLE THREAD IMAGING APPARATUS HAVING A LIGHT SEAL MEANS BETWEEN THE LIGHT ASSEMBLY MEANS AND THE THREAD

[75] Inventors: Samuel C. Domenico, Golden; Thomas S. Lincoln, Arvada, both of Colo.

[73] Assignee: Coors Brewing Company, Golden, Colo.

[21] Appl. No.: 678,666

[22] Filed: Apr. 1, 1991

Related U.S. Application Data

[62] Division of Ser. No. 445,975, Dec. 4, 1989, Pat. No. 5,045,688.

[51] Int. Cl.⁵ .............................................. H01J 40/14
[52] U.S. Cl. .................................. 250/223 B; 356/240
[58] Field of Search ................... 250/223 B; 356/240; 209/526

[56] References Cited

U.S. PATENT DOCUMENTS

| | | | |
|---|---|---|---|
| 4,435,641 | 3/1984 | Hajime | 250/223 B |
| 4,758,084 | 7/1988 | Tokumi et al. | 250/223 B |
| 4,786,801 | 11/1988 | Shay | 356/240 |

Primary Examiner—David C. Nelms
Assistant Examiner—Que T. Le
Attorney, Agent, or Firm—Klaas, Law, O'Meara & Malkin

[57] ABSTRACT

A bottle thread inspection apparatus for inspecting a bottle thread arranged in a generally spiral configuration about the periphery of a bottle neck having a central longitudinal axis comprising: A light source for illuminating the bottle thread; a mirror assembly for reflecting light received from the bottle thread into an imaging lens assembly; an imaging lens assembly for focusing a full-length image of the bottle thread on a unitary image plane; a signal generating means for generating a data signal representative of the image of the bottle thread focused on the unitary image plane; and a data analysis device for analyzing the data signal based upon predetermined criteria for detecting flaws in the bottle thread.

10 Claims, 6 Drawing Sheets

BOTTLE THREAD IMAGING APPARATUS HAVING A LIGHT SEAL MEANS BETWEEN THE LIGHT ASSEMBLY MEANS AND THE THREAD

This application is a division of application Ser. No. 445,975, filed Dec. 4, 1989, now U.S. Pat. No. 5,045,688.

BACKGROUND OF THE INVENTION

The present invention relates generally to method and apparatus for inspecting the thread portion of a bottle and, more particularly, to an automated method and apparatus for inspecting bottle thread which enables high-speed processing of a plurality of bottles.

Returnable bottles, if they are to be reused by a manufacturer, must be inspected for flaws prior to reuse. Screw-on-cap type bottles are especially susceptible to damage in the thread region. To date, most thread inspection has been performed by human inspectors due to the difficulty of adequately inspecting the entire length of a bottle thread with automated devices.

Figures 1, 2, 3, 4:
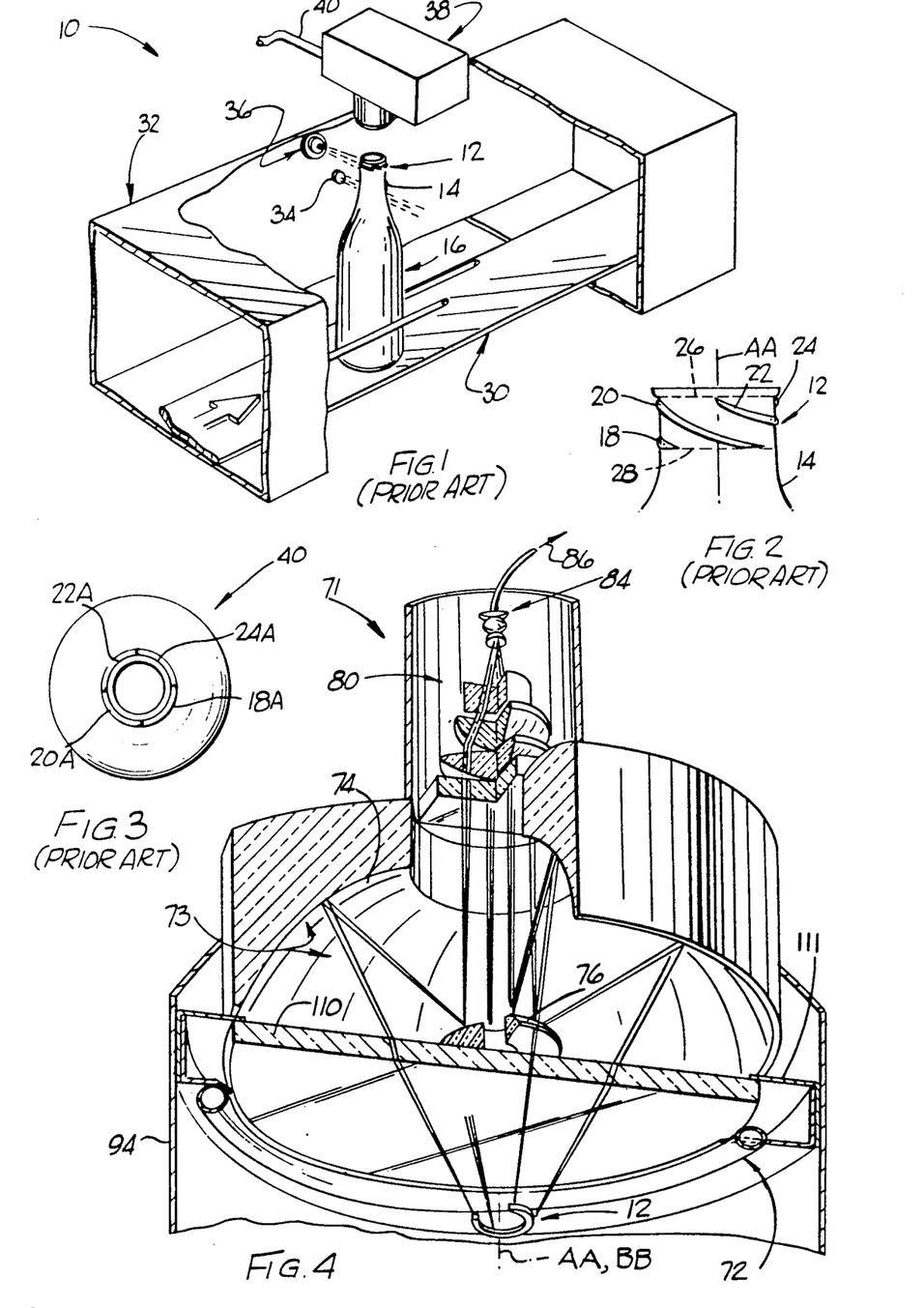
FIG. 1 is a schematic, perspective illustration of a prior art bottle thread inspection apparatus.
FIG. 2 is a side elevation view illustrating the thread configuration of a prior art bottle.
FIG. 3 is a plan view of an image of the type produced by a prior art bottle thread inspection apparatus.
FIG. 4 is a cutaway perspective view of a bottle thread imaging assembly.

A typical prior art bottle, as illustrated in FIG. 2, may have a thread portion 12 which consists of four separate "threads" or "leads" 18, 20, 22, 24 arranged symmetrically about the bottle central longitudinal axis AA. In one exemplary glass beverage bottle construction, the outer surface of the neck portion upon which the bottle thread is mounted has a radius, of 1.050 inches. Each of the threads in positioned within a cylindrical region on the bottle neck defined by an upper border 26 and a lower border 28 which are separated by an axial distance of approximately 0.14 inches. Each thread or lead 18, 20, 22, 24 begins at upper border 26 and terminates at lower border 28 and extends at a helix angle of 6° 31'. The thread travel about the circumference of this exemplary bottle is 108° which provides a total length of 0.370 inches for each lead. Each of the leads begins at a point spaced 90° from the next adjacent lead and terminates at a point spaced 90° from the termination point of the next adjacent thread. Each lead has a generally uniform, dome-shaped cross section (not shown) having a radius of curvature at its outer surface of approximately 0.016 inches.

A prior art inspection apparatus 10 adapted to inspect the thread portion 12 of a series of identical bottles 16 (only one shown) is illustrated in FIG. 1. Inspection apparatus 10 includes a bottle conveyor system 30 positioned within a light shielding enclosure 32. The conveyor 30 moves the bottles through an inspection station comprising a triggering light beam 34, at least one flash lamp 36, and a camera 38. When a bottle 16 is positioned directly below camera 38, the bottle neck 14 intersects triggering light beam 34 which simultaneously actuates flash lamps 36 and camera 38. The camera 38 produces an image 40 of the bottle top such as illustrated in FIG. 3. Image 40 includes only a partial image 18A, 20A, 22A, 24A of each bottle thread 18, 20, 22, 24. The partial image consists of an image of the top half of the first circumferentially measured 90° of each thread. The remainder of each bottle thread is obscured from the camera's field of view due to the position of the camera and due to the fact that each of the threads overlap approximately 18° when viewed from above. The lower portion of each bottle thread image 18A, 20A, 22A, 24A is also somewhat out of focus with respect to the upper portion thereof due to the fact that the upper and lower portions of the thread are positioned at different distances from the camera and due to the fact that the camera is positioned very close to the bottle thread, e.g. one inch from the uppermost portion of each lead. An electronic data signal representative of image 40 is analyzed by a machine vision system based upon predetermined criteria for detecting flaws in the portion of the image 40 associated with each thread lead 18, 20, 22, 24. Since the image 18A, 20A, 22A, 24A of each thread lead provided in image 40 is not a complete image, the corresponding data analysis will not detect flaws associated with the obscured portion of each lead.

SUMMARY OF THE INVENTION

The present invention is directed to method and apparatus for high-speed, on-line, automated inspection of the thread portion of a plurality of bottles and for other article inspection applications.

Thus, the invention may comprise a bottle thread inspection apparatus for inspecting a bottle thread arranged in a generally spiral configuration about the periphery of a bottle neck having a central longitudinal axis comprising: (a) light source means for illuminating said bottle thread; (b) mirror means for reflecting light received from said bottle thread into imaging lens means; (c) imaging lens means for focusing an image of said bottle thread on a unitary image plane; (d) signal generating means for generating a data signal representative of said image of said bottle thread focused on said unitary image plane; and (e) data analysis means for analyzing said data signal based upon predetermined criteria for detecting flaws in said bottle thread.

The invention may also comprise a method for inspecting bottle thread comprising: (a) illuminating the bottle thread; (b) reflecting light received from the entire length of the bottle thread into a light focusing assembly; (c) focusing the reflected light received by the light focusing assembly onto a unitary image plane so as to provide a planar image of the entire bottle thread thereon; and (d) analyzing the planar image of the bottle thread to detect flaws in the bottle thread.

The invention may also comprise a method for analyzing objects which are provided at a predetermined locus on the sidewalls of articles of the type comprising a central longitudinal axis and an annular, generally axially symmetrical sidewall comprising the steps of: (a) moving a series of the articles along a path extending perpendicular to the longitudinal axes of the articles; (b) illuminating each article at a predetermined position along the path; (c) during the illumination of each article receiving light from the object associated with the article in a mirror assembly positioned axially adjacent to the article and reflecting the light received from the object into a lens assembly; (d) using the reflected light from the mirror assembly, focusing an image of the object on a unitary image plane; (e) generating a data signal representative of the image of the object focused on the unitary image plane; (f) analyzing the data signal according to predetermined criteria.

The invention may also comprise an article inspection apparatus for inspecting articles of the type having a sidewall generally symmetrically positioned about a central longitudinal axis of the article wherein the portion of the article to be inspected comprises an object which is provided at a predetermined, common object location on the sidewall of each article, comprising: (a) article conveyance means for continuously moving a single file series of said articles along an inspection path which extends perpendicular to the central longitudinal axes of each of the articles positioned thereon; (b) illumination means positioned along said inspection path in physically noninterfering relationship with said articles conveyed along said inspection path for illuminating each article as it passes through an inspection station along the path; (c) mirror means fixedly located at said inspection station for reflecting light from a 360° band portion on said sidewall of the article which includes said object into a lens means during said continuous movement of said articles along said inspection path; (d) lens means for focusing light from said 360° band portion of said article sidewall which includes said object on a unitary image plane for forming an image of said object on said image plane; (e) data signal generating means for generating a data signal representative of said image of said object; and (f) data analysis means for analyzing said data signal based upon predetermined criteria.

The invention may also comprise a bottle thread imaging apparatus for use in high-speed inspection of bottle thread provided on a plurality of generally identically shaped bottles, comprising: (a) conveying means for continuously conveying a series of bottles in single file relationship along a bottle inspection path; (b) imaging means fixedly positioned adjacent to said bottle inspection path in noninterfering relationship with bottles moving therealong for focusing a distorted, full-length image of said bottle thread on a unitary image plane.

The invention may also comprise a bottle thread imaging apparatus for generating an image of a bottle thread comprising: (a) light source means for emitting light of a predetermined limited wavelength range selected to be substantially totally reflected by the exterior surface of said bottle; (b) imaging means for receiving light from said light source means which is reflected from said bottle thread for forming an image of said bottle thread.

The invention may also comprise a bottle thread imaging apparatus for generating an image of a bottle thread comprising: interior light source means light-sealingly isolated from the exterior surface of the bottle thread for illuminating the bottle thread from the inside out; and (b) imaging means for receiving light from said light source means which has passed through said bottle thread for forming an image of said bottle thread.

BRIEF DESCRIPTION OF THE DRAWINGS

An illustrative and presently preferred embodiment of the invention is shown in the accompanying drawings in which.

DETAILED DESCRIPTION OF THE INVENTION

The Invention in General

Figure 5:
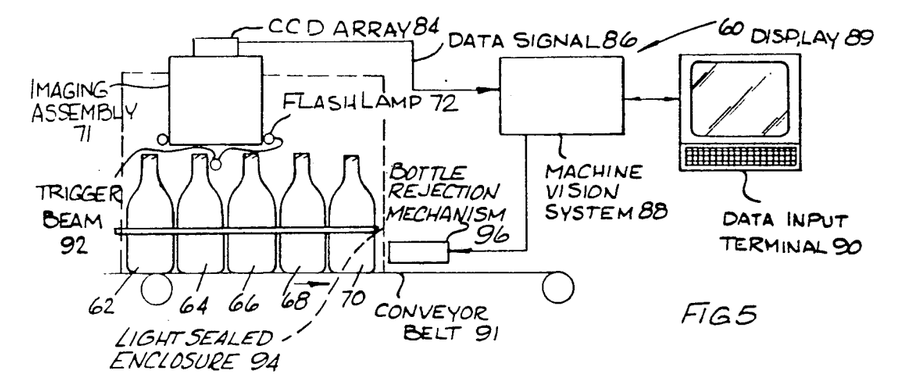
FIG. 5 is a schematic illustration of a bottle thread inspection apparatus.

A bottle thread inspection apparatus 60 is illustrated schematically in FIG. 5. The apparatus 60 is adapted for high-speed inspection of the thread portion of a plurality of bottles 62, 64, 66, 68, 70 passing therethrough in single file relationship. Each of the bottles comprises an identical bottle configuration having bottle thread and neck portions 12, 14 which may be identical to those described above with respect to FIG. 2. The bottle inspection apparatus 60, includes a light source means such as annular flash lamp 72 which directs light onto the surface of bottle thread 12. Light reflected from the bottle thread is received by an imaging assembly 71 which produces an image of bottle thread 12.

The thread imaging assembly 71, as shown in FIG. 4, comprises mirror assembly 73 which includes concave mirror surface 74 and convex mirror surface 76 for reflecting light received from the bottle thread into an imaging lens assembly. The imaging lens assembly 80 focuses a full-length, full-width, distorted image 82, FIG. 6, of bottle thread 12 onto a unitary image plane XX, FIG. 9. A signal generating means such as a two-dimensional image sensor array, which may be a CCD array 84, generates a data signal 86 representative of the image 82 of the bottle thread. Data analysis means such as machine vision system 88 with display terminal 89 and data input terminal 90 analyze the data signal based upon predetermined criteria for detecting flaws in the bottle thread 12. The imaging assembly 71 and flash lamp 72 are positioned within a light-sealed enclosure 94 such that only light from lamp 72 is used for imaging.

The bottle thread imaging assembly 71, in the preferred embodiment illustrated in FIG. 5, is used in association with a conveying means such as conveyor belt 91 which continuously moves a series of bottles arranged in single file relationship along an inspection path through enclosure 94. The inspection path extends perpendicular to the central longitudinal axes AA of each of the bottles. The conveyor belt 91 moves continuously, sequentially positioning each of the bottles below the bottle thread imaging assembly 71. A flash lamp triggering means, such as a conventional photoelectric trigger beam 92 which is positioned at the same elevation as the neck of each bottle, is provided for triggering flash lamp 72 at the instant when a bottle is positioned in coaxial alignment with the imaging assembly 71. In one embodiment, the data analysis means 88, upon detection of a flawed bottle, sends a reject signal to a conventional bottle reject mechanism 96. The reject mechanism is actuated by the reject signal to remove the associated defective bottle from the conveyor belt 91.

Figure 6:
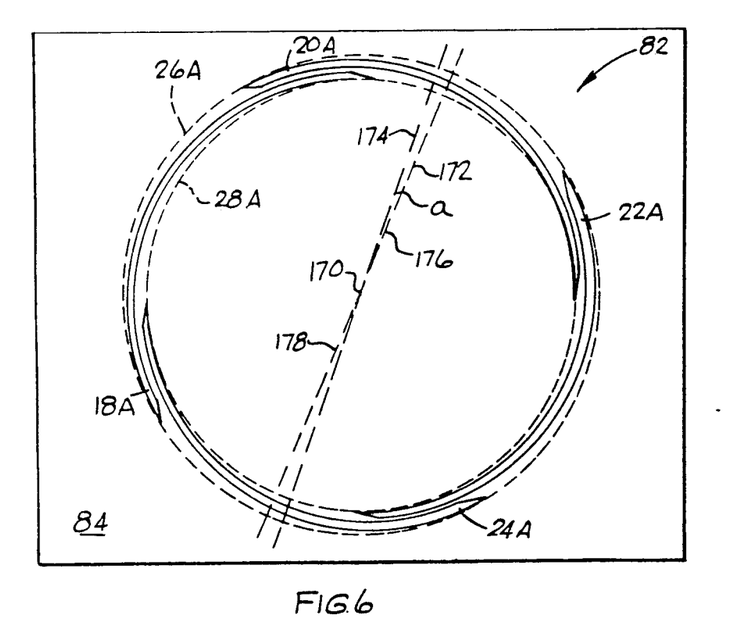
FIG. 6 is a top plan view of a CCD array of the bottle thread imaging assembly of FIG. 4 with an image of a bottle thread provided thereon.
Figure 7:
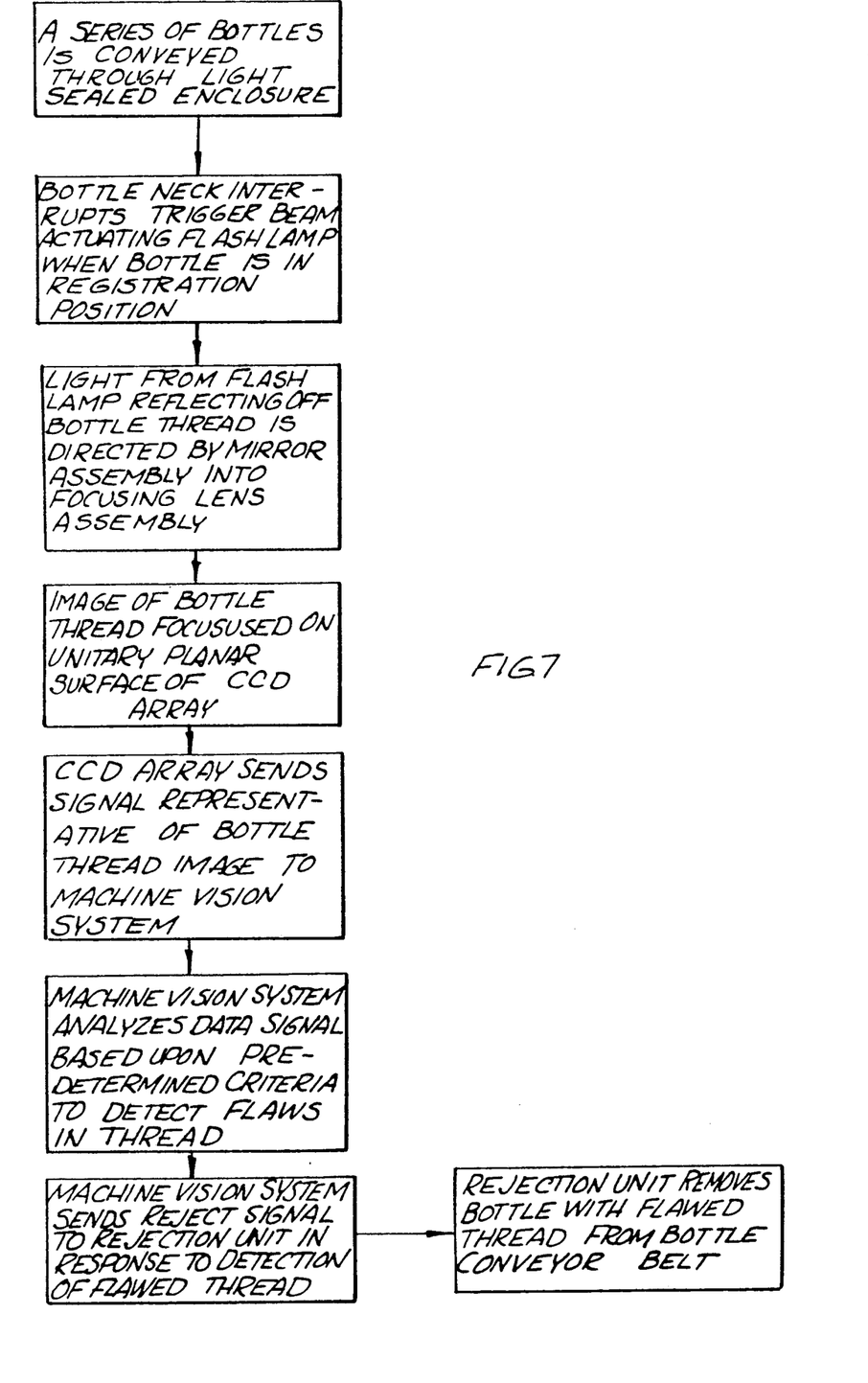
FIG. 7 is a block diagram illustrating the operation of a bottle thread inspection apparatus of the type illustrated in FIG. 5.

In operation of the invention, as illustrated in FIG. 7, a series of bottles are conveyed in single file relationship by conveyor belt 91 through the light-sealed enclosure 94. At a position whereat a bottle is in coaxial alignment with the central longitudinal axis BB of imaging assembly 71, the neck of the bottle interrupts trigger beam 92 actuating flash lamp 72. Light from flash lamp 72 is reflected off bottle thread 12 and is thereafter directed by mirror surfaces 74, 76 into the imaging lens assembly 80, FIG. 4. The imaging lens assembly focuses a distorted image 82 of the bottle thread 12 onto a unitary image plane XX coincident with the planar face surface of CCD array 84, FIG. 6. The CCD array 84 then sends a data signal 86 representative of image 82 of the bottle thread to a machine vision system 88. The machine vision system analyzes the data representative of the thread image based upon predetermined criteria to detect flaws in the associated bottle thread 12. Upon detection of a flawed thread, the machine vision system 88 sends a reject signal to rejection unit 96 which removes the bottle with the flawed thread from conveyor belt 91.

Having thus described the bottle thread inspection apparatus 60 and method of operation thereof in general, certain specific features of the apparatus will now be described in further detail.

Bottle Thread Imaging Assembly

Figure 8:
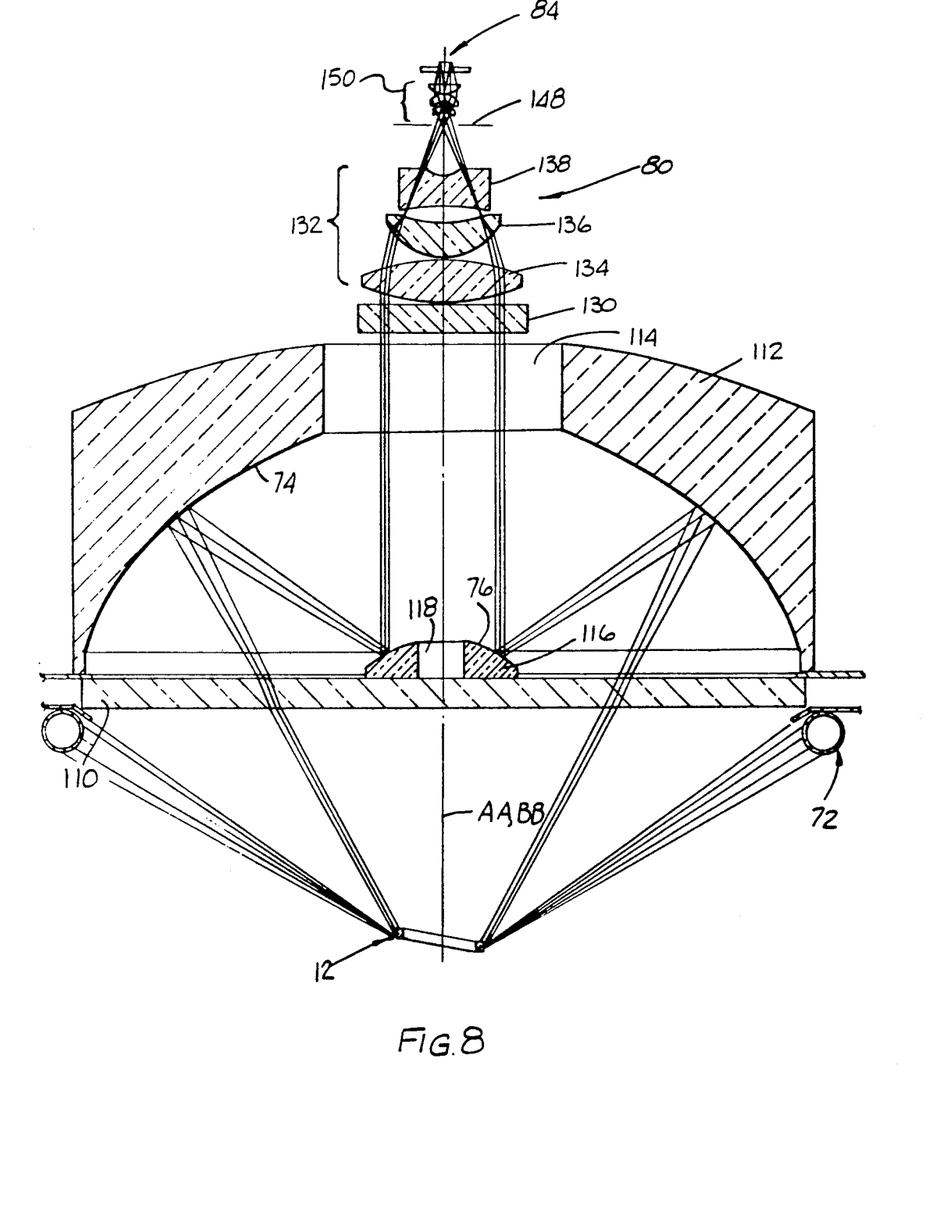
FIG. 8 is a cutaway elevation view of the bottle imaging assembly of FIG. 4.
Figure 9:
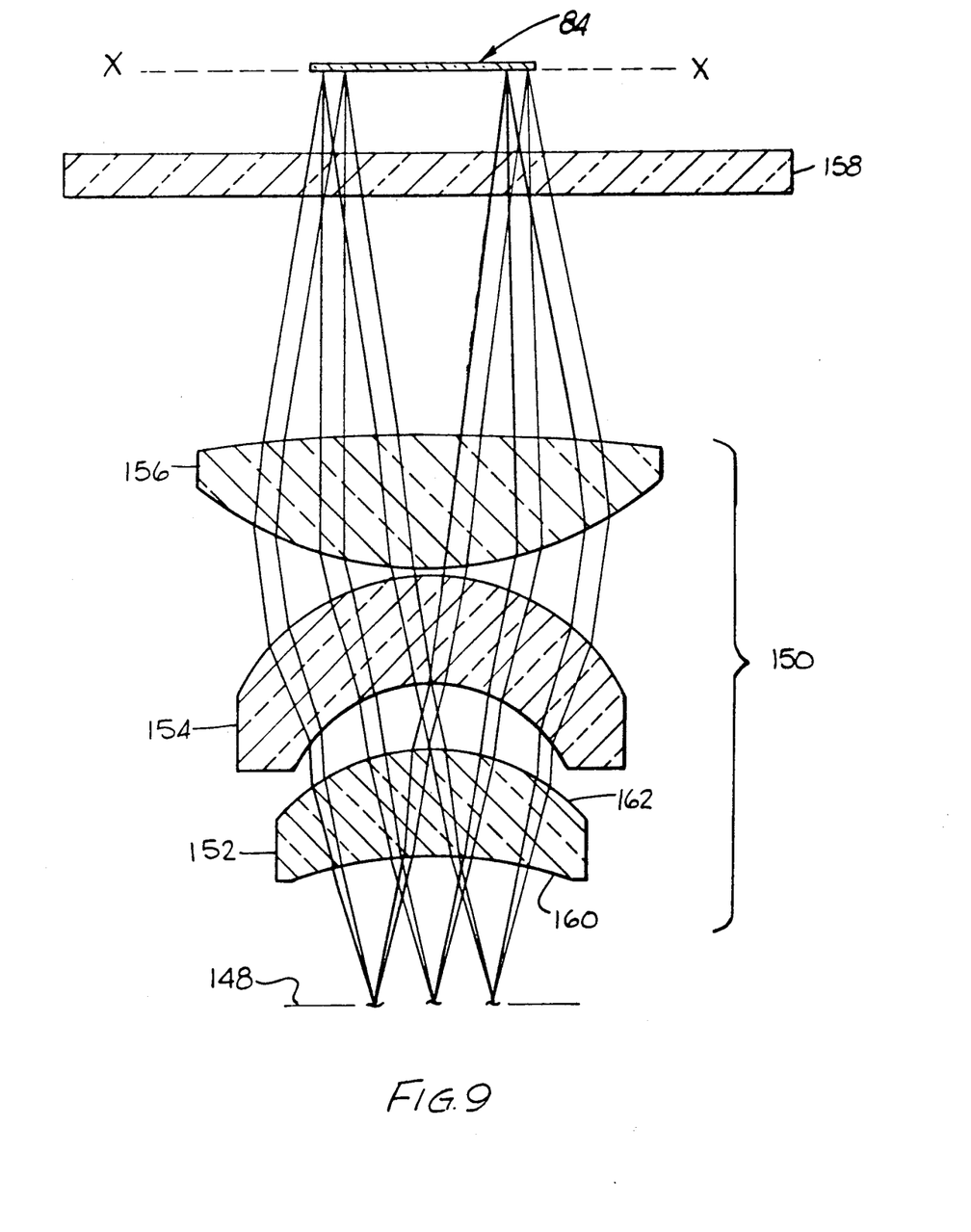
FIG. 9 is a detail elevation view of a portion of the bottle imaging assembly of FIG. 4.

Bottle thread imaging assembly 71, FIGS. 4, 8 and 9, may comprise a transparent sealing plate 110 which is mounted on support structure such as walls of sealing enclosure 94 by suitable support members 111. The transparent sealing plate may comprise an optical-quality clear glass plate having a central longitudinal axis BB and having a thickness of 9.52 mm which is positioned such that a lower planar surface thereof is perpendicular to the longitudinal axis AA of each bottle passing therebelow. The plate may be positioned at a distance of 2.5 mm above the the aligned bottle.

A generally dome-shaped first mirror member 112 is supported on plate 110 at a peripheral portion thereof. Mirror member 12 may have a lower, convex mirror surface 74 and may have a central bore 114 extending therethrough which is coaxial with the central longitudinal axis BB of transparent sealing plate 110.

A second mirror member 116 having a generally dome-shaped convex mirror upper surface 76 and having a central bore 118 extending therethrough is supported at a lower portion thereof on the sealing plate 110 and is positioned in coaxial alignment with the sealing plate and first mirror member 112. The two dome-shaped mirror surfaces 74, 76 provide a reflective assembly of a type generally referred to in the optical arts as a "Schwarzschild", see, e.g., U.S. Pat. No. 4,205,902 of David R. Shafer entitled LASER BEAM EXPANDER, which is hereby incorporated by reference for all that is disclosed therein.

In a generally cylindrical region positioned directly above central bore 114 in the second mirror member, there is positioned a light filter 130; a first refractive lens group 132 comprising a first lens element 134, a second lens element 136, and a third lens element 138; an aperture stop 148 which may have an opening diameter of 2.5 mm; a second refractive lens group 150, FIGS. 8 and 9, comprising a fourth lens element 152, a fifth lens element 154, and a sixth lens element 156; a second light filter 158; and a CCD array 84. CCD array 84 is positioned in coplanar relationship with a lens assembly image plane XX. Each lens element comprises a front surface 160 positioned relatively nearer the bottle-to-be-imaged and a back surface 162 positioned relatively more remotely from the bottle. Parameters of the various lens elements for a specific embodiment adapted to produce an image of a bottle thread of the type described above with reference to FIG. 2 is indicated below in Table I.

TABLE I*

| OPTICAL ELEMENT | FRONT SURFACE RADIUS | FRONT SURFACE AXIAL POSITION | BACK SURFACE RADIUS | BACK SURFACE AXIAL POSITION |
|---|---|---|---|---|
| MIRROR SURFACE 74 | −123.75000 | −73.25 | (MIRROR) | N/A |
| MIRROR SURFACE 76 | −35.34500 | 100.00 | (MIRROR) | N/A |
| PLATE 130 | INF | 9.525 | INF | 1.000 |
| LENS 134 | 62.68500 | 12.700 | −76.71000 | 0.500 |
| LENS 136 | 20.43000 | 12.000 | 52.01000 | 4.620 |
| LENS 138 | −119.20000 | 11.000 | 12.43500 | 17.250 |
| LENS 152 | −9.57500 | 2.225 | −4.41500 | 1.350 |
| LENS 154 | −3.25000 | 2.175 | −4.70000 | 0150 |
| LENS 156 | 7.57500 | 2.750 | −37.09000 | 4.850 |

*NOTE: Radii are given in units of mm. A positive radius indicates a center of curvature positioned above the surface; a negative radius indicates a center of curvature positioned below the surface
Axial position is given in units of mm and indicates the distance between the subject surface and the next optical surface in the light path at central axis BB. A positive distance indicates the next optical surface in the light path is positioned above the subject surface; a negative distance indicates the next optical surface is positioned below the subject surface.

SIGNAL GENERATING MEANS AND DATA ANALYSIS MEANS

FIG. 6 is a top plan view of CCD array 84 and the image of a bottle thread 12 which is focused thereon by imaging assembly 71. As shown by FIG. 6, the thread image 82 comprises a full-length, full-width, distorted image 18A, 20A, 22A, 24A of each of the individual threads 18, 20, 22, 24. The images of the individual threads are located within a ring-shaped space having an outer border 26B and an inner border 28B corresponding generally to the upper and lower cylindrical borders 26, 28 of the bottle region in which threads 18, 20, 22, 24 are located. As is well-known in the art, a CCD array provides a data signal indicative of light received thereby, in this case light corresponding to the image 82 of bottle thread 12. In a preferred embodiment of the invention utilizing the above-described imaging assembly 71, the CCD array 84 comprises a 6.28 mm × 4.78 mm array with 774 × 242 pixels resolution.

The data signal produced by CCD array 84 is representative of image 82. Depending upon the type of CCD array which is used, the data signal may represent image 82 in a gray scale format wherein each pixel is represented by one of a relatively broad range of values, e.g. 0–63, or may represent image 82 in binary format wherein each pixel is represented by one of two possible values. Various techniques for analyzing an image data signal are known in the art. For example, one method of image analysis for detecting thread flaws is to compare the data image actually generally to an ideal data image template which is representative of unflawed bottle threads. In such an image comparison system, it is necessary to utilize an algorithm to rotate the data image to a standard orientation prior to comparing the actual data image to the data image template. Such rotation algorithms are known in the art. A machine vision system capable of performing such an analysis is described in detail in Menardi et al., U.S. patent application Ser. No. 285,518 filed Dec. 14, 1988, now U.S. Pat. No. 4,919,799, which is hereby specifically incorporated by reference for all that is disclosed therein. Such a machine vision system, Model MVP-2000, and manuals describing the use and programming thereof are available from Itran Corporation, having a business address of 670 North Commercial Street, Manchester, N.H., 03101.

Another method of data signal analysis which is presently the best mode contemplated for detecting flaws in bottle threads, such as those described in FIG. 2, which have bilateral symmetry about any diametric plane extending through the bottle will now be described. In this embodiment, a data image of the bottle thread corresponding to image 82 is stored and manipulated by the machine vision system. The data image may be either a gray scale or binary image. Although analysis beams, 172, 174, etc., are shown projected onto image 82 in FIG. 6 for purposes of explanation, it is to be understood that the below-described analysis is performed upon electronically stored data which is representative of image 82. Initially, the center of the data image is determined as by algorithmically extending straight lines (not shown) between opposite outer peripheral tips of each thread image. The point of intersection of such lines defines the center 170 of the image 82. Next, a series of diametric lines 172, 174 are algorithmically projected from center 170 outwardly through the ring region 264, 274 in which the image of each bottle thread lies. Such diametric lines are projected around the entire 360° of the circle having a center at 170 in increments "a" of, e.g., 5°. Each of the diametrically projected beams 72, 74, etc., comprises a first radially extending portion 176 and an opposite second radially extending portion 178. For each diametric beam, the pixel value of the first radial portion 176 in the region thereof located in the ring area defined by 26B and 28B is compared to the pixel value of the second radial portion 178 located in the ring area. Due to the symmetry of the image 82, the two pixel values thus compared should be identical if the associated thread portions are unflawed except in the unlikely situation of two flawed thread regions occurring in diametrically opposite positions of the thread patterns. Thus, if the pixel values of the two compared radii of each diameter vary by more than some predetermined amount, e.g. 0, the vision system interprets this deviation as a flaw in the associated portion of the bottle thread. If the number of diametrical analysis beams indicating a thread flaw exceed a predetermined number, e.g. 1, then the vision system determines the bottle to be defective and, based upon this determination, issues a rejection signal to the bottle reject mechanism 96.

ALTERNATIVE EMBODIMENTS

In an alternative embodiment of the invention (not shown), an assembly similar in construction to the bottle thread inspection apparatus 60 having an imaging assembly similar in construction to that described with respect to imaging assembly 71 shown in FIGS. 4, 8 and 9, is used for reading alphanumeric characters or other indicia which are printed on the sidewall of cylindrical containers or other articles, such as cones, which are annularly symmetrical. Problems with reading alphanumeric characters printed on the sidewalls of cylindrical containers are described in detail in Menardi et al., U.S. patent application Ser. No. 285,518, incorporated by reference above. In order to use the above-described inspection apparatus 60 for reading alphanumeric characters printed on predetermined band regions of a cylindrical containers, it would be necessary to modify the conveyor system of apparatus 60 so as to separate the cylindrical containers sufficiently, e.g. 2 inches, so as to enable all surface portions of the band containing the alphanumeric-characters-to-be-read to be exposed to light from annular light source 72. To the extent that the band region containing the alphanumeric-characters-to-be-read is positioned at a different axial distance from plate 110 than the axial distance of the bottle thread configuration 22 and to the extent that the alphanumeric-characters-to-be-read on the cylindrical container are positioned on a cylindrical surface of different diameter than the diameter of the neck region 14 of bottle 16, and to the extent that the alphanumeric-characters-to-be-read are at a different axial height than bottle region 26, 28, then modifications would be required in the various optical components of the imaging assembly 71 and in the size of the CCD array 84 in order to accommodate a differently sized image of the band region of the cylindrical container on the CCD array or in order to provide proper focus of that image. If alphanumeric-characters-to-be-read, such as those described in Menardi et al., are printed in a band region of a cylindrical container which may also contain other alphanumeric characters or other graphic indicia, it would also be necessary to provide a registration indicia, either directly in the band region containing the alphanumeric characters to be read or in a closely adjacent region on the cylindrical container sidewall, so as to enable the vision system to be provided with a reference point for angularly orienting the planar ring image of the cylindrical sidewall band portion containing the alphanumeric characters. In a preferred embodiment, this registration indicia may comprise a bar code indicia printed within the small-width band region containing the alphanumeric characters, the bar code indicia preferably progressing in a circumferential direction such that a circumferential scan of the ring image would readily reveal the position of the bar code indicia and thus the angular orientation of that ring image. In this embodiment, once the vision system had identified the bar code region of the ring image, an appropriate algorithm is used to identify the exact circumferential portion of the ring image containing the alphanumeric characters to be identified. Thereafter, a template matching system employing templates corresponding to the distorted image of each alphanumeric character to be recognized is employed for identifying the image of each character provided in the selected circumferential region of the ring image. Such an apparatus obviates the need for orienting the alphanumeric-characters-to-be-read directly opposite from a camera and thus eliminates the need for spinning containers about their longitudinal axes to achieve such angular registration. Such a system could, of course, also be used to recognize or compare objects (either indicia such as alphanumeric characters or physical objects such as bottle thread, etc.) to predetermined norms for purposes such as character recognition or flaw detection on nearly any series of identically shaped articles, e.g. cylinders, cones, spheres, toruses, etc., having annular symmetry about a central longitudinal axis which are serially positioned in coaxial alignment with an imaging assembly such as imaging assembly 71 described above. Articles having shapes approaching such annular symmetry, e.g. articles with regular polygonal cross sections such as squares, octagons, etc., or articles with nearly circular, ellipse-shaped cross sections may also be inspectable by an imaging assembly such as 71 with some loss of resolution as compared to articles with true annular symmetry. Articles with true annular symmetry and articles having shapes approaching annular symmetry may be collectively referred to herein as being "generally" annularly symmetrical.

Figure 10:
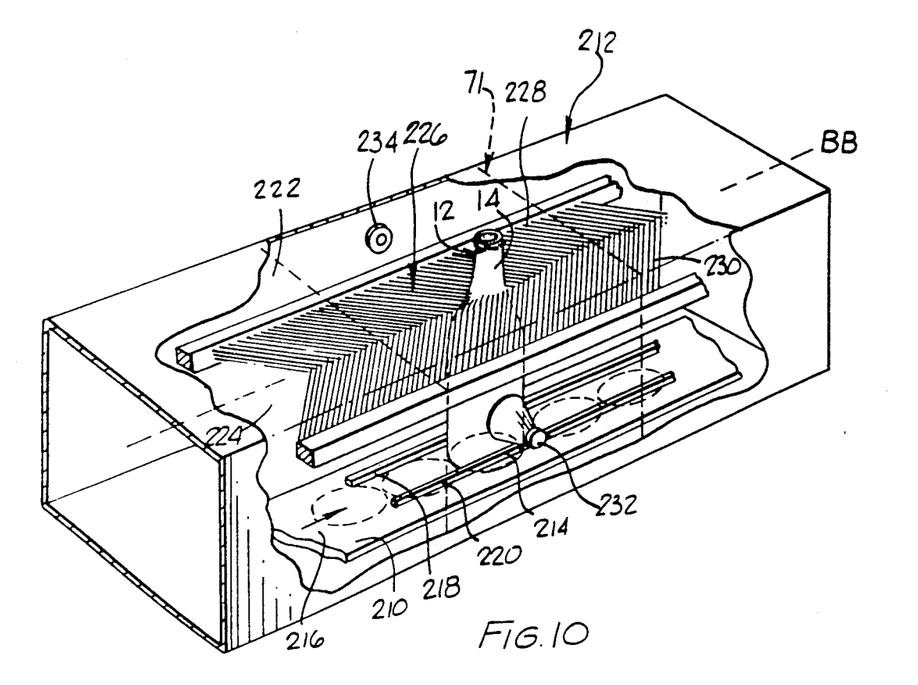
FIG. 10 is a perspective, schematic illustration of an alternative embodiment of a bottle thread inspection apparatus.

In another embodiment of the invention such as illustrated in FIG. 10, a conveyor belt 210 passing through a light-sealed enclosure 212 and supporting a plurality of adjacently positioned bottles 214 (only one shown) thereon moves the bottles along a bottle path 216, defined by a pair of stationary guide rails 218, 220, which passes below a bottle thread imaging assembly 71 (only the position is indicated in FIG. 10) which may be identical to that described with reference to FIGS. 4, 8 and 9 above. In this embodiment of the invention, the light-sealed enclosure 212 is divided into an upper enclosure portion 222 and a lower enclosure portion 224 which are light-sealingly separated from one another by light-sealing brush assembly 226 which is positioned at the same elevation as a lower portion of the bottle neck 14. The brush assembly 226 may be provided by a first set of horizontal, forwardly angled brushes 228 and a second set of horizontal, forwardly angled brushes 230 which intersect along a line BB which is aligned with bottle path 216. In this embodiment of the invention, a plurality of flash lamps 232 (only one shown) are positioned on either side of the bottle path at a position directly below the location of imaging assembly 71. A trigger beam device 234, which may be identical to that described above with reference to FIG. 5, actuates the flash lamps 232. The flash lamps directly illuminate the lower portion of the bottle, i.e. the bottle portion in lower light chamber portion 224. Light passing through the lower sidewall portion of the bottle is reflected upwardly therewithin and is thereafter transmitted outwardly through the bottle neck 14 and bottle thread 12 into the imaging assembly 71. Due to the greater thickness of the glass in the bottle thread portion in comparison to the remainder of the glass in the bottle neck, the image associated with the bottle thread portion 12 which is produced on CCD array 84 contrasts sharply with the image of the surrounding portion of the bottle neck. This method of bottle light generation is presently the best mode contemplated for illuminating the bottle thread 12. Such an illumination method may overcome problems associated with partial light penetration of translucent objects and resulting light reflection from underlying bottle surfaces which is experienced when external light reflected from the outer surface of the thread 12 is used to provide the thread image 82.

In yet another embodiment of the invention which is also adapted to overcome problems of partial light penetration, an identical flash lamp assembly to that described with reference to FIGS. 4, 8 and 9 and reference numeral 72 is employed, except that the light source, rather than being a white light source, is an infrared light source or a light source of another wavelength which is substantially totally reflected by the exterior surface of the particular bottle threads which are to be inspected. In such an assembly, the transparent sealing plate 110 and various lens assembly components must be constructed from a material which readily transmits light of the infrared or other selected wavelength.

Figure 11:
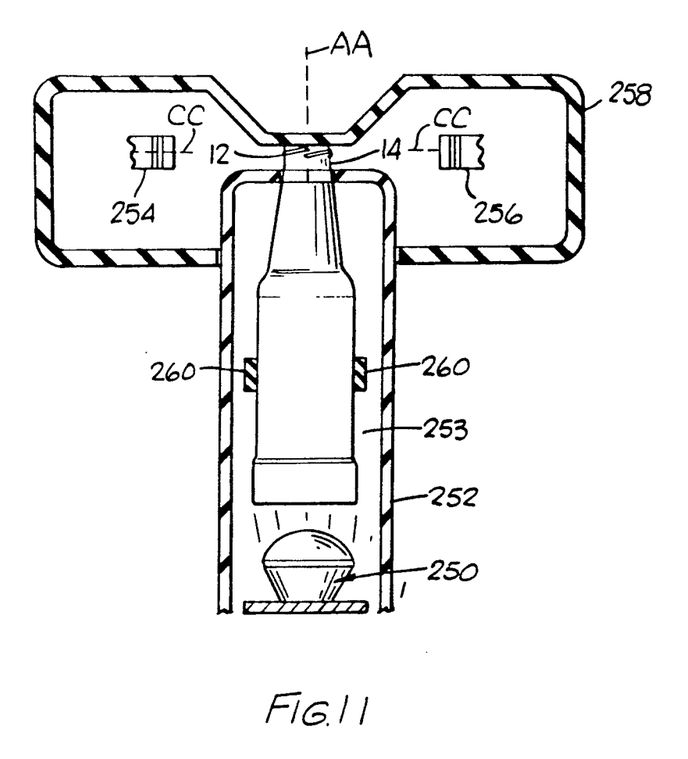
FIG. 11 is a front, cross sectional view of another alternative embodiment of a bottle thread inspection apparatus.

Another assembly for providing interior bottle illumination is illustrated in FIG. 11 in which a stationary flash lamp 250, or alternatively a continuously-on high intensity lamp, is mounted beneath a moving bottle conveyor assembly 252 of a type having an inverted U-shaped cross section defining an inverted U-shaped enclosure 253. This conveyor assembly may be constructed in a clampshell-type configuration adapted for clamping about the necks of a series of bottles which are to be conveyed thereby. This arrangement effectively isolates each bottle neck region 14 from the light applied to a lower portion of the bottle except to the extent that light is actually transmitted through an interior portion of the bottle to the bottle neck. A pair of stationarily mounted cameras 254, 256 are positioned laterally adjacent to the bottle neck. The cameras comprise lines of sight CC which extend generally perpendicular to the direction of conveyor movement. The cameras 254, 256 are mounted in a light-sealed enclosure 258 which may make brushing contact with the moving conveyor 252 and the upper portion of bottles mounted in the conveyor. A spin belt 260 is provided which spins each bottle about the longitudinal axis AA thereof as it passes through the field of view of cameras 254, 256. A triggering device (not shown), which may be identical to the trip beam-type actuators described above, actuates each camera a plurality of times, e.g. twice as the bottle passes through its field of vision. Each bottle undergoes a predetermined amount of angular displacement about its longitudinal axis AA, e.g. 90°, between camera actuations such that all surfaces of the bottle neck are imaged by the cameras 254, 256 during the multiple camera actuations. Thus, for example, four images of each bottle thread 12 may be provided by this assembly. Each image is thereafter analyzed, e.g. by template comparison, to detect flaws in the thread image portion which is captured thereby.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A bottle thread imaging apparatus for generating an image of a bottle thread comprising:
   a) light assembly means positioned entirely outside of said bottle and for illuminating the bottle thread from the inside out;
   b) light seal means for light-sealingly isolating the exterior surface of the bottle thread from light from said light assembly means other than light passing through said bottle from inside out; and
   c) imaging means for receiving light from said light assembly means which has passed through said bottle thread for forming an image of said bottle thread.

2. The invention of claim 1 wherein said light assembly means is positioned adjacent a lower portion of said bottle and wherein said light sealing means is positioned above said light assembly means in encompassing relationship with said bottle.

3. The invention of claim 2 wherein said light shield means comprises a brush assembly.

4. The invention of claim 2 wherein said light assembly means is positioned adjacent a lateral sidewall of the bottle.

5. The invention of claim 2 wherein said light assembly means is positioned adjacent a bottom wall of the bottle.

6. A bottle thread imaging apparatus for generating images of a bottle threads comprising:

conveyor means for conveying a series of bottles in single file relationship;

stationary light assembly means positioned entirely outside of said bottles and adjacent said conveyor means in noninterefering relationship with said bottles conveyed by said conveyor means for illuminating the bottle thread from the inside out; and light seal means for light-sealingly isolating the exterior surface of said bottle threads from light from said light assembly means other than light passing through said bottle from inside out;

imaging means for receiving light from said light assembly means which has passed through said bottle thread for forming an images of said bottle threads.

7. The invention of claim 6 wherein said light assembly means is positioned adjacent a lower portion of bottles on said conveyor means and wherein said light sealing means is positioned above said light assembly means in encompassing relationship with each bottle passing said light assembly means.

8. The invention of claim 6 wherein said light shield means comprises a brush assembly.

9. The invention of claim 6 wherein said light assembly means is positioned at a location adjacent lateral sidewalls of bottles moving along said conveyor means.

10. The invention of claim 6 wherein said light assembly means is positioned at a location adjacent bottom walls of bottles moving along said conveyor means.

* * * * *